United States Patent
Kleyman

(10) Patent No.: US 9,526,520 B2
(45) Date of Patent: *Dec. 27, 2016

(54) SURGICAL ACCESS METHOD AND ASSEMBLY INCLUDING SLEEVE AND PORT

(71) Applicant: Covidien LP, Mansfield, MA (US)

(72) Inventor: Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/679,451

(22) Filed: Apr. 6, 2015

(65) Prior Publication Data

US 2015/0209075 A1    Jul. 30, 2015

Related U.S. Application Data

(63) Continuation of application No. 14/244,978, filed on Apr. 4, 2014, now Pat. No. 9,022,927, which is a (Continued)

(51) Int. Cl.
*A61B 17/02* (2006.01)
*A61B 17/34* (2006.01)

(52) U.S. Cl.
CPC ....... *A61B 17/3423* (2013.01); *A61B 17/0218* (2013.01); *A61B 17/3431* (2013.01); (Continued)

(58) Field of Classification Search
CPC . A61B 17/02; A61B 17/0218; A61B 17/0293; A61B 17/3423; A61B 17/3466; A61B 17/347; A61B 17/3445; A61B 17/3431
(Continued)

(56) References Cited

U.S. PATENT DOCUMENTS 3,347,227 A   10/1967  Harrower
5,906,577 A   5/1999   Beane et al.
(Continued)

FOREIGN PATENT DOCUMENTS

EP    0950376 A1    10/1999
EP    1774918 A1    4/2007
(Continued)

OTHER PUBLICATIONS

European Search Report EP08253236 dated Feb. 10, 2009.
(Continued)

*Primary Examiner* — Todd E Manahan
*Assistant Examiner* — Jessica Weiss

(57) ABSTRACT

A surgical access assembly includes a sleeve and a port. The sleeve is adapted for insertion within tissue to access an underlying tissue site. The sleeve defines a first passage therethrough. The first passage has a first diameter. The port defines one or more second passages extending therethrough. The port is adapted for insertion within the first passage of the sleeve in a substantially sealed relationship therewith. The one or more second passages are adapted for a substantially sealed reception of a surgical object therethrough. The one or more second passages have one or more second diameters. The port is selectively removably positionable within the first passage of the sleeve. The first diameter is greater than the one or more second diameters.

11 Claims, 3 Drawing Sheets

Related U.S. Application Data continuation of application No. 13/030,178, filed on Feb. 18, 2011, now Pat. No. 8,821,390.

(60) Provisional application No. 61/323,102, filed on Apr. 12, 2010.

(52) U.S. Cl.
CPC . *A61B 2017/0225* (2013.01); *A61B 2017/347* (2013.01); *A61B 2017/3429* (2013.01); *A61B 2017/3445* (2013.01); *A61B 2017/3466* (2013.01)

(58) Field of Classification Search
USPC ...... 600/101, 104, 106, 201–249; 604/96.01, 604/104–109, 164.01, 167, 523
See application file for complete search history.

(56) References Cited

U.S. PATENT DOCUMENTS

| | | | |
|---|---|---|---|
| 6,033,426 A | 3/2000 | Kaji | |
| 6,254,534 B1 | 7/2001 | Butler et al. | |
| 6,382,211 B1 | 5/2002 | Crook | |
| 6,440,063 B1 | 8/2002 | Beane et al. | |
| 6,450,983 B1 | 9/2002 | Rambo | |
| 6,582,364 B2 | 6/2003 | Butler et al. | |
| 6,589,167 B1 | 7/2003 | Shimomura et al. | |
| 6,723,044 B2* | 4/2004 | Pulford | A61B 17/0293 128/850 |
| 6,945,932 B1 | 9/2005 | Caldwell et al. | |
| 7,214,185 B1 | 5/2007 | Rosney et al. | |
| 7,377,898 B2 | 5/2008 | Ewers et al. | |
| 7,445,597 B2 | 11/2008 | Butler et al. | |
| 7,559,893 B2 | 7/2009 | Bonadio et al. | |
| 7,798,898 B2 | 9/2010 | Luciano, Jr. et al. | |
| 8,821,390 B2* | 9/2014 | Kleyman | A61B 17/3423 600/203 |
| 9,022,927 B2* | 5/2015 | Kleyman | A61B 17/3423 600/206 |
| 2001/0037053 A1 | 11/2001 | Bonadio et al. | |
| 2003/0014076 A1 | 1/2003 | Mollenauer et al. | |
| 2004/0267096 A1 | 12/2004 | Caldwell et al. | |
| 2005/0020884 A1 | 1/2005 | Hart et al. | |
| 2005/0090822 A1 | 4/2005 | DiPoto | |
| 2005/0203346 A1 | 9/2005 | Bonadio et al. | |
| 2006/0084842 A1 | 4/2006 | Hart et al. | |
| 2006/0149306 A1 | 7/2006 | Hart et al. | |
| 2006/0161049 A1 | 7/2006 | Beane et al. | |
| 2006/0161050 A1 | 7/2006 | Butler et al. | |
| 2006/0229501 A1 | 10/2006 | Jensen et al. | |
| 2006/0247498 A1 | 11/2006 | Bonadio et al. | |
| 2006/0247499 A1 | 11/2006 | Butler et al. | |
| 2006/0247500 A1 | 11/2006 | Voegele et al. | |
| 2006/0247673 A1 | 11/2006 | Voegele et al. | |
| 2007/0093695 A1 | 4/2007 | Bonadio et al. | |
| 2007/0151566 A1 | 7/2007 | Kahle et al. | |
| 2007/0185387 A1 | 8/2007 | Albrecht et al. | |
| 2007/0255219 A1 | 11/2007 | Vaugh et al. | |
| 2008/0021359 A1 | 1/2008 | Beckman et al. | |
| 2008/0027476 A1 | 1/2008 | Piskun | |
| 2008/0200767 A1 | 8/2008 | Ewers et al. | |
| 2008/0255519 A1 | 10/2008 | Piskun et al. | |
| 2009/0036745 A1 | 2/2009 | Bonadio et al. | |
| 2009/0093752 A1* | 4/2009 | Richard | A61B 17/3423 604/24 |
| 2009/0221966 A1 | 9/2009 | Richard | |
| 2009/0326330 A1 | 12/2009 | Bonadio et al. | |
| 2009/0326332 A1 | 12/2009 | Carter | |
| 2010/0010449 A1 | 1/2010 | Leibowitz et al. | |
| 2010/0081882 A1 | 4/2010 | Hess et al. | |
| 2010/0249525 A1* | 9/2010 | Shelton, IV | A61B 17/3423 600/208 |
| 2010/0249526 A1* | 9/2010 | Shelton, IV | A61B 17/0293 600/208 |
| 2011/0124967 A1 | 5/2011 | Morgan | |
| 2011/0166423 A1 | 7/2011 | Farascioni et al. | |
| 2011/0251463 A1 | 10/2011 | Kleyman | |
| 2011/0251464 A1 | 10/2011 | Kleyman | |
| 2011/0251465 A1 | 10/2011 | Kleyman | |
| 2011/0251466 A1 | 10/2011 | Kleyman et al. | |
| 2011/0313250 A1 | 12/2011 | Kleyman | |
| 2012/0130184 A1 | 5/2012 | Richard | |
| 2012/0149987 A1 | 6/2012 | Richard et al. | |

FOREIGN PATENT DOCUMENTS

| | | |
|---|---|---|
| EP | 2044889 A1 | 4/2009 |
| WO | 97/33520 | 9/1997 |
| WO | 99/16368 | 4/1999 |
| WO | 2004/075741 | 9/2004 |
| WO | 2006040748 A1 | 4/2006 |
| WO | 2008/042005 | 4/2008 |

OTHER PUBLICATIONS

European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
European Search Report from EP Application No. EP 11250454 mailed Jan. 9, 2014.
Canadian Office Action issued in corresponding Canadian Appln. No. 2,733,370 dated Aug. 26, 2016.

* cited by examiner

SURGICAL ACCESS METHOD AND ASSEMBLY INCLUDING SLEEVE AND PORT

CROSS REFERENCE TO RELATED APPLICATIONS

The present application is a continuation of U.S. application Ser. No. 14/244,978, filed Apr. 4, 2014, which is a continuation of U.S. application Ser. No. 13/030,178, filed Feb. 18, 2011, now U.S. Pat. No. 8,821,390, which claims the benefit of U.S. Provisional Application Ser. No. 61/323,102, filed on Apr. 12, 2010, the entire contents of each of which are incorporated herein by reference.

TECHNICAL FIELD

The present disclosure relates generally to a surgical access assembly and method for use in minimally invasive surgical procedures, such as endoscopic or laparoscopic type procedures, and more particularly to a surgical access method and assembly including a sleeve and port for providing access to a body cavity.

BACKGROUND

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gases are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various access devices with valves and seals are used during the course of minimally invasive procedures and are widely known in the art. However, a continuing need exists for surgical access devices that can facilitate the accessibility of an underlying tissue site with relative ease and with minor inconvenience for the surgeon.

SUMMARY

The present disclosure is directed to a surgical access assembly that includes a sleeve and a port. The sleeve includes a sleeve body having first and second ends. The sleeve body may be formed of a flexible material and the first and second ends may be formed of one or more of a rigid and a semi-rigid material. The sleeve is adapted for insertion within tissue to access an underlying tissue site. The sleeve defines a first passage therethrough. The first passage permits unsealed access to the underlying tissue site. The first passage has a first diameter.

The port defines one or more second passages extending therethrough. The port is adapted for insertion within the first passage of the sleeve in a substantially sealed relationship therewith. The one or more second passages are adapted for a substantially sealed reception of a surgical object therethrough. The one or more second passages have one or more second diameters. The port is selectively removably positionable within the first passage of the sleeve. The first diameter is greater than the one or more second diameters. One or both of the sleeve and the port may be substantially hourglass-shaped.

In embodiments, one or more clamps may operably couple the sleeve and the port. The one or more clamps are repositionable between clamped and unclamped configurations. The one or more clamps may include one or more locking elements. The one or more locking elements are adapted to lock the sleeve and the port together when positioned in the clamped configuration.

In one aspect, the present disclosure is directed to a method of accessing an underlying tissue site. The method includes providing a surgical access assembly that includes a sleeve and a port. The sleeve defines a first passage therethrough. The first passage has a first diameter. The port defines one or more second passages extending therethrough. The one or more second passages define one or more second diameters. The one or more second diameters are smaller than the first diameter. The method includes selectively positioning the sleeve in an incision or a natural orifice of a patient; selectively positioning the port within the first passage of the sleeve; and selectively accessing the underlying tissue site through one or more of the first passage and the one or more second passages. The method may include advancing a surgical object through the one or more second passages in a substantially sealed relationship therewith. In one respect, the method includes selectively removing the port from the sleeve. In another respect, the method may include inserting the sleeve within a Hasson incision. The method may include inserting the sleeve within a patient to access the colon. The method may include coupling the sleeve and the port with a clamp so that the sleeve and port are in a locked position relative to one another. In one respect, the method includes withdrawing a specimen through the first passage of the sleeve.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
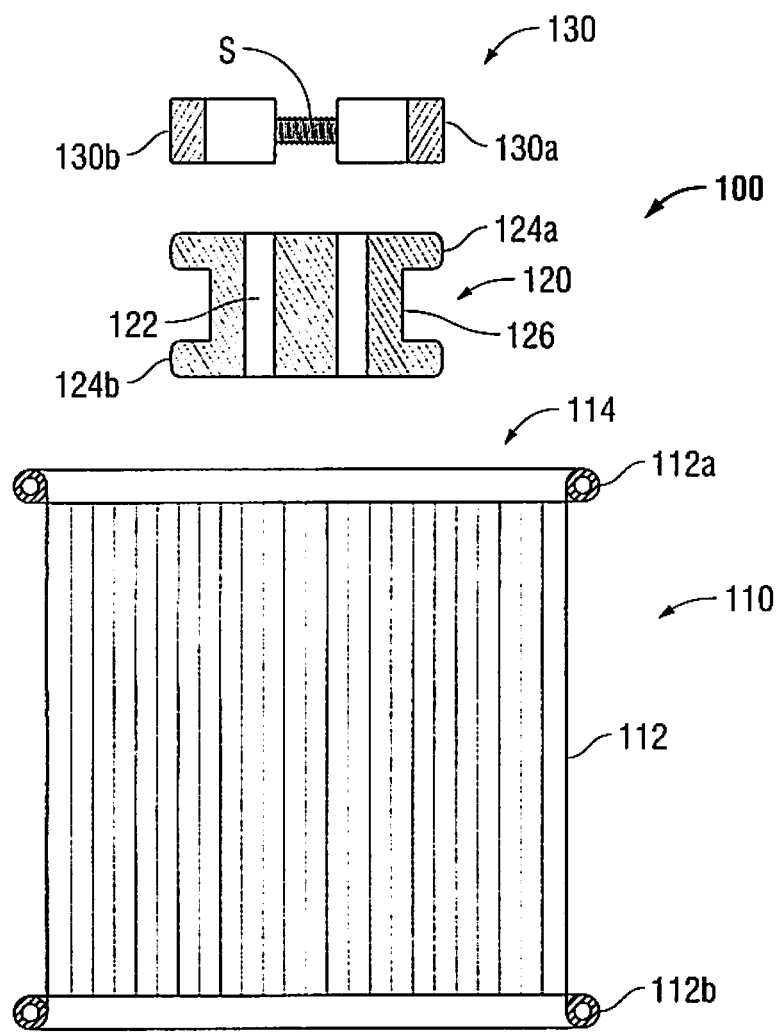
FIG. 1 is an exploded, cross-sectional view, with parts separated, of one embodiment of a surgical access assembly in accordance with the present disclosure.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

One type of minimal invasive surgery described herein is multiple instrument access through a single surgical port. This technique is a minimally invasive surgical procedure, which permits a surgeon to operate through a single entry point, typically the patient's navel. The disclosed procedure involves insufflating the body cavity and positioning a housing member within an opening in the patient's skin (e.g., an incision or a naturally occurring orifice). Instruments including an endoscope and additional instruments such as graspers, staplers, forceps or the like may be introduced within the port to carry out the surgical procedure.

Referring now to the drawings, in which like reference numerals identify identical or substantially similar parts throughout the several views, FIG. 1 illustrates a surgical access assembly 100 that includes a sleeve 110 and a port 120. The sleeve 110 includes a sleeve body 112 having first and second ends 112a, 112b on respective proximal and distal ends of the sleeve body 112 that are integrally formed with the sleeve body 112. The sleeve body 112 may be formed of a flexible material, e.g., elastomeric material such as rubber or any other suitable material in order to conform to the tissue tract "TT" (FIG. 3) of an incision or natural orifice. Alternatively, the sleeve body 112 may be formed of an inflexible material and may conform to the tissue tract "TT" (FIG. 3) of an incision or natural orifice by virtue of a biasing force of the port, as will be explained further below.

In embodiments, the first and second ends 112a, 112b, which may be annular rings 112a, 112b, may be formed of a rigid and/or a semi-rigid material, e.g., a polymeric material or any other suitable material. For example, the first and second ends 112a, 112b may include annular rings 112a, 112b that are formed of a material that is semi-rigid such that the leading annular ring 112b may be deformed for insertion into an incision or opening in the body, and that is resiliently biased towards its initial position so as to retain the sleeve within the incision or opening once placed therewithin. In addition, the first end 112a may include an annular ring that is formed of a material that is semi-rigid such that the trailing annular ring may be, e.g., rolled, over the sleeve 112 in order to retract the incision before during or after insertion of the port therewithin. The first ring 112a may have any number of different shapes, e.g., cross-sectional shapes, for, e.g., providing gripping surfaces to a user, for improving the ability of the sleeve to resist un-rolling, to improve the ability of the ring to be rolled. Alternatively, a simple ring 112a having a circular or substantially circular cross-section may be employed.

Figure 3:
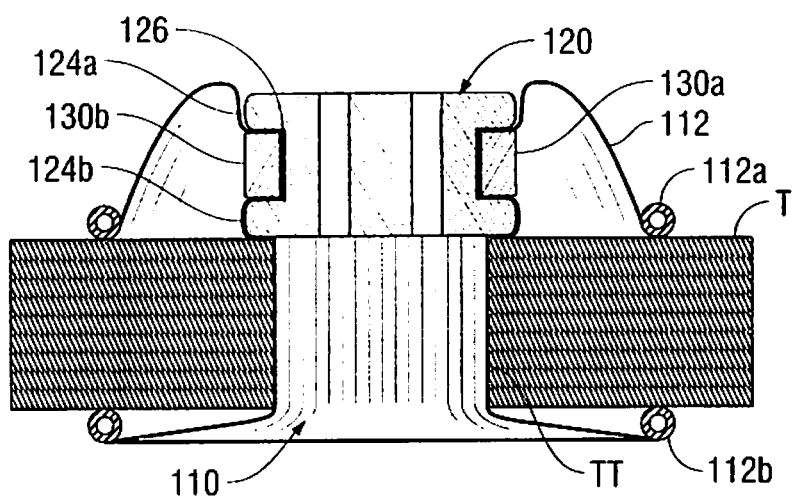
FIG. 3 is a cross-sectional view of the surgical access assembly of FIG. 1 shown positioned within tissue.

As best shown in FIG. 3, the sleeve 110 is adapted for insertion within tissue "T" to access an underlying tissue site "TS", e.g., through the abdominal or peritoneal lining in connection with a laparoscopic surgical procedure. The sleeve 110 defines a first passage 114 therethrough. The first passage 114 permits unsealed access to the underlying tissue site "TS." The first passage 114 has a first diameter that is adapted to accommodate the port 120 therein.

Figure 4:
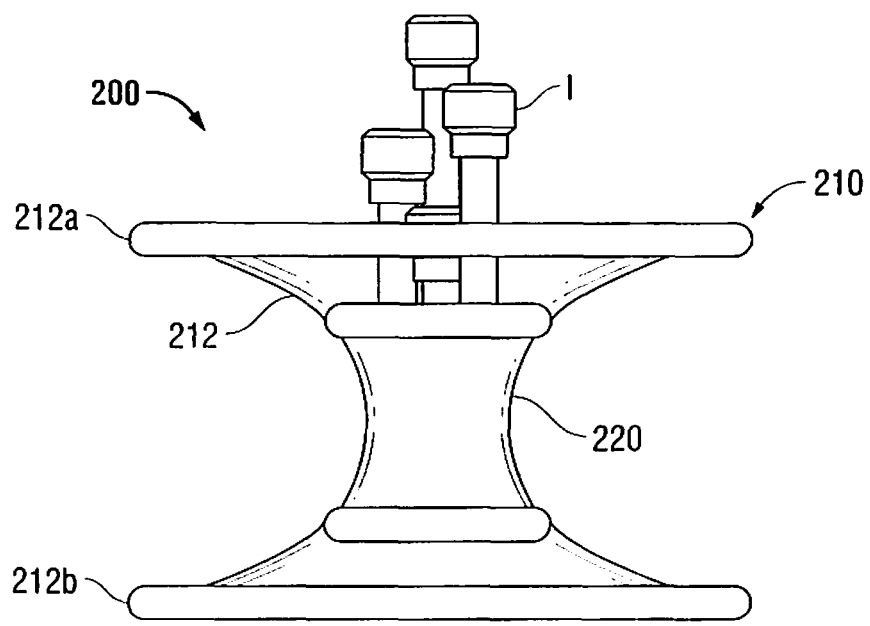
FIG. 4 is a side view of another embodiment of a surgical access assembly with a plurality of instruments shown positioned therein in accordance with the present disclosure.
Figure 5:
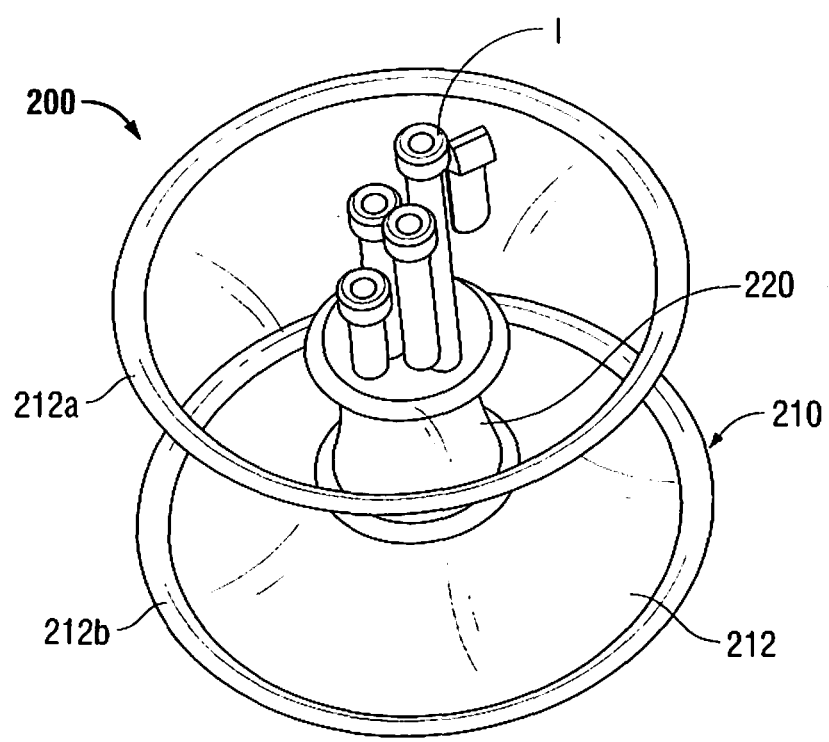
FIG. 5 is a top, perspective view of the surgical access assembly of FIG. 4 with the plurality of instruments shown positioned therein.

The port 120 defines one or more second passages 122 extending therethrough. One type of port that may be employed is disclosed and illustrated in Applicant's U.S. Provisional Patent Appl. Ser. No. 60/997,885, filed Oct. 5, 2007, the entire contents of which are hereby incorporated by reference herein. The port 120 is adapted for insertion within the first passage 114 of the sleeve 110 in a substantially sealed relationship therewith when sleeve 110 is inserted through an opening in tissue "T". The one or more second passages 122 are adapted for a substantially sealed reception of a surgical object "I" (FIGS. 4 and 5) therethrough, e.g., a cannula or other type of surgical instrument. The one or more second passages 122 may have one or more second diameters in order to accommodate variously-sized surgical objects "I" (FIGS. 4 and 5) in a substantially sealed relationship therewith. The first diameter is greater than the one or more second diameters so that the port 120 can be selectively removably positioned within the first passage 114 of the sleeve 110. The port 120 may be made from a disposable, compressible, and/or flexible type material such as a suitable foam or gel material having sufficient compliance to form a seal about one or more surgical objects "I" (FIGS. 4 and 5). The foam is preferably sufficiently compliant to accommodate off axis motion of the surgical object. In one embodiment, the foam includes a polyisoprene material. In embodiments, the material may be elastomeric.

Figure 2:
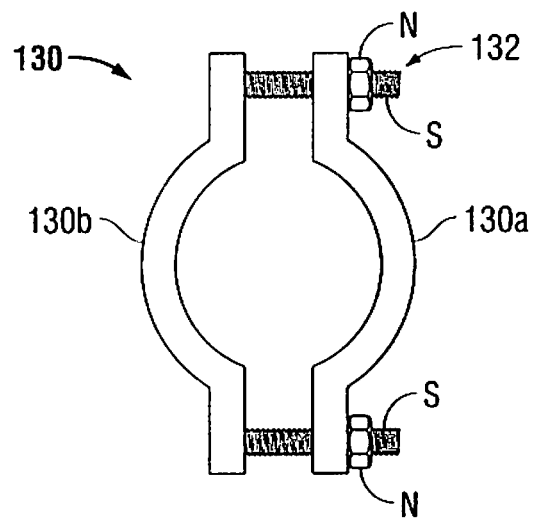
FIG. 2 is a top plan view of one embodiment of a clamp in accordance with the present disclosure.

Referring now to FIGS. 2 and 3, one or more clamps 130 may operably couple the sleeve 110 and the port 120. The one or more clamps 130 are repositionable between clamped (FIG. 3) and unclamped (FIG. 2) configurations. As shown in FIG. 2, the one or more clamps 130 may include one or more locking elements 132, e.g., a screw "S" and nut "N" and first and second sections 130a, 130b. With reference to FIG. 3, the one or more locking elements 132 are adapted to lock the sleeve 110 and the port 120 together when positioned in the clamped configuration. In particular, the screw "S" may be tightened through screw holes (not shown) defined within each of the first and second sections 130a, 130b until the sleeve body 112 is secured to the port 120. As best shown in FIG. 3, the first and second sections 130a, 130b may be adapted to be secured within a channel 126 defined about the circumference of the port 120 between upper and lower lips 124a, 124b thereof.

In use of the surgical access assemblies 100, the sleeve 110, 210 is selectively positioned to a predetermined depth in an incision, e.g., a navel incision or a Hasson incision, or a natural orifice of a patient, which may include the anus and the vagina in order to selectively access the underlying tissue site "TS" (e.g., colon, uterus, etc.) through the first passage 114. The port 120 may then be selectively positioned within the first passage 114 of the sleeve 110 in order to selectively access the underlying tissue site "TS" through the one or more second passages 122. In the embodiment shown in FIGS. 1-3, the port 120 is configured to be positioned outside of the incision (see FIG. 3), such that the distal face of the port 120 rests against the outer wall of the patient's body. As illustrated in FIG. 3, the clamp 130 may then be used to couple the sleeve 110 and the port 120 so that the sleeve 110, 210 and the port 120, 220 are in a locked position relative to one another. A surgical object "I" may then be advanced through the one or more second passages 122 in a substantially sealed relationship therewith, and where necessary, insufflation fluid, e.g., $CO_2$, may be introduced into the underlying tissue site "TS" with one or more of the surgical objects "I" in order to create a working space in the underlying tissue site "TS." Should the clinician need to access the underlying tissue site "TS" through a larger diameter, e.g., to remove a specimen therefrom, the clinician may then readily selectively disconnect the clamp 130 and remove the port 120 from the sleeve 110 to gain access again through the first passage 114.

As illustrated in FIGS. 4 and 5, one embodiment of a surgical access assembly is generally designated as 200. In this embodiment, the surgical access assembly 200 includes a sleeve 210 and a port 220. The sleeve 210 includes a sleeve body 212 having first and second ends 212a, 212b on respective proximal and distal ends of the sleeve body 212 that are integrally formed with, or otherwise connected to, the sleeve body 212. One or both of the sleeve 210 and the port 220 may be substantially hourglass-shaped. Alternatively, the port 220 may be hourglass-shaped while the sleeve 212 may be generally cylindrical when in an inoperative position.

In use of the surgical access assemblies 200, the sleeve 210 is selectively positioned to a predetermined depth in an incision, e.g., a navel incision or a Hasson incision, or a natural orifice of a patient, which may include the anus and the vagina in order to selectively access the underlying tissue site "TS" (e.g., colon, uterus, etc.) through the first passage 114. The port 220 may then be selectively positioned within the first passage 114 of the sleeve 110, 210 in order to selectively access the underlying tissue site "TS" through the one or more second passages 122. Unlike the embodiment shown in FIGS. 1-3, in which the clamp 130 is used to couple the sleeve 110 and the port 120 so that the sleeve 110 and the port 120 are in a locked position relative to one another, in this embodiment, the port 220 is maintained in position by the biasing force of the port 220 expanding outwardly after being compressed to fit within the incision or opening. More specifically, in the absence of the incision or opening, the port 220 is not securely attached or fixed in any way relative to the sleeve 210, but rather is completely free to move relative to the sleeve 210. The sleeve 210 does not engage the port 220, but rather is trapped between the wall of the incision or opening and the sidewall of the flexible port. Advantageously, the port 220 is dimensioned so as to extend fully through the thickness of the patient's incision or opening, e.g., such that the upper portion of the port 220 is positioned above the outer wall of the incision or opening, the middle region of the port 220 is positioned within the incision or opening, and the lower portion of the port 220 is positioned below the lower wall of the incision or opening, thereby insuring that the port 220 will be maintained in position within the incision or opening and provide adequate sealing at all locations within the incision or opening. A surgical object "I" may then be advanced through the one or more second passages 122 in a substantially sealed relationship therewith, and where necessary, insufflation fluid, e.g., $CO_2$, may be introduced into the underlying tissue site "TS" with one or more of the surgical objects "I" in order to create a working space in the underlying tissue site "TS." Should the clinician need to access the underlying tissue site "TS" through a larger diameter, e.g., to remove a specimen therefrom, the clinician may then readily selectively remove the port 220 from the sleeve 210, to gain access again through the first passage 114. In addition, if desired, the clinician may then replace the port 220 within the sleeve 210 and continue with other aspects of the surgical procedure with the port 220 in place in the sleeve 210 and within the incision or opening.

In embodiments of the present disclosure, surgical access assemblies 100, 200 may come preassembled with the port 120, 220 disposed within the sleeve 110, 210. In the alternative, the port 120, 220 may be positioned within sleeve 110, 210 at the surgical site as discussed above.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

The invention claimed is:

1. A surgical access device, comprising:
    a sleeve having a distal end and a proximal end, the sleeve including a first ring supported on the proximal end of the sleeve and a second ring supported on the distal end of the sleeve, the first ring rollable to shorten a longitudinal length of the sleeve and exert a retraction force against tissue surrounding the sleeve; and
    a flexible port defining an opening therethrough, the opening configured for sealed reception of a surgical object therethrough, the flexible port including proximal and distal ends, the proximal end of the flexible port having an upper lip and the distal end of the flexible port having a lower lip, the flexible port positionable within the sleeve such that the upper lip of the flexible port is disposed externally of a body cavity, the lower lip of the flexible port is disposed internally of the body cavity, and the proximal and distal ends of the flexible port are disposed between the proximal and distal ends of the sleeve, wherein the flexible port is maintained between the proximal and distal ends of the sleeve by a biasing force exerted by the flexible port on the sleeve.

2. The surgical access device of claim 1, wherein the flexible port has an hourglass shape.

3. The surgical access device of claim 1, wherein the flexible port includes foam.

4. The surgical access device of claim 1, wherein the flexible port defines a plurality of openings therethrough, each opening of the plurality of openings configured for sealed reception of a surgical object.

5. The surgical access device of claim 1, wherein the flexible port includes a compressible material, the flexible port transitionable between a compressed condition and an expanded condition, the flexible port insertable into a retracted body opening while the flexible port is in the compressed condition, the flexible port configured to press against an inner surface of the sleeve to form a seal with tissue that forms the body opening while the flexible port is in the expanded condition and exerting the biasing force on the sleeve.

6. The surgical access device of claim 1, wherein the opening defined by the flexible port is configured for sealed reception of a trocar cannula.

7. A method for accessing a body cavity, the method comprising:
    inserting a sleeve into a body opening;
    extending a distal end of the sleeve through the body opening such that the distal end of the sleeve is internally disposed within the body cavity;
    positioning a proximal end of the sleeve externally disposed relative to the body cavity;
    rolling the proximal end of the sleeve to shorten a longitudinal length of the sleeve;

compressing a flexible port to fit within an opening of the sleeve;

positioning lower and upper lips of the flexible port between the proximal and distal ends of the sleeve such that the lower lip of the flexible port is internally disposed within the body cavity and the upper lip of the flexible port is externally disposed relative to the body cavity; and expanding the flexible port to exert a biasing force on an inner surface of the sleeve to form a seal against tissue forming the body opening.

8. The method of claim 7, further including advancing a surgical object through an opening defined in the flexible port and into the body cavity.

9. The method of claim 7, wherein rolling the proximal end of the sleeve includes rolling a ring supported on the proximal end of the sleeve.

10. A method for accessing a body cavity, the method comprising:

inserting a sleeve into a body opening;

extending a distal end of the sleeve through the body opening such that the distal end of the sleeve is internally disposed within the body cavity;

positioning a proximal end of the sleeve externally disposed relative to the body cavity;

rolling the proximal end of the sleeve to exert a retraction force against the tissue surrounding the sleeve to retract the body opening;

compressing a flexible port to fit within an opening of the sleeve;

positioning lower and upper lips of the flexible port between the proximal and distal ends of the sleeve such that the lower lip of the flexible port is internally disposed within the body cavity and the upper lip of the flexible port is externally disposed relative to the body cavity; and expanding the flexible port to exert a biasing force on an inner surface of the sleeve to form a seal against tissue forming the body opening.

11. The method of claim 10, wherein rolling the proximal end of the sleeve includes rolling a ring supported on the proximal end of the sleeve.

* * * * *